US010905814B2

(12) United States Patent
Brehm

(10) Patent No.: US 10,905,814 B2
(45) Date of Patent: Feb. 2, 2021

(54) VIDEO-BASED UPGRADE OF DIALYSIS MACHINES

(71) Applicant: Fresenius Medical Care Deutschland GmbH, Bad Homburg (DE)

(72) Inventor: Winfried Brehm, Hofheim (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 16/299,729

(22) Filed: Mar. 12, 2019

(65) Prior Publication Data

US 2019/0314568 A1   Oct. 17, 2019

(30) Foreign Application Priority Data

Apr. 16, 2018   (DE) .................. 10 2018 108 941

(51) Int. Cl.

| | |
|---|---|
| *G06F 3/0481* | (2013.01) |
| *A61M 1/28* | (2006.01) |
| *A61M 1/16* | (2006.01) |
| *G06F 3/041* | (2006.01) |
| *G16H 40/63* | (2018.01) |

(52) U.S. Cl.
CPC .............. *A61M 1/28* (2013.01); *A61M 1/16* (2013.01); *G06F 3/041* (2013.01); *A61M 2205/505* (2013.01); *G06F 3/0481* (2013.01); *G16H 40/63* (2018.01)

(58) Field of Classification Search
USPC ........................................... 710/72
See application file for complete search history.

(56) References Cited

U.S. PATENT DOCUMENTS

| | | | | |
|---|---|---|---|---|
| 4,812,125 A | * | 3/1989 | Strashun | G09B 5/065 434/219 |
| 5,307,263 A | * | 4/1994 | Brown | A61B 5/0022 600/301 |
| 5,788,851 A | * | 8/1998 | Kenley | A61M 1/14 210/739 |
| 5,995,987 A | * | 11/1999 | Iida | G05B 19/056 700/18 |
| 7,263,710 B1 | | 8/2007 | Hummel, Jr. et al. | |
| 8,321,044 B2 | * | 11/2012 | Plahey | G16H 40/63 700/94 |
| 9,189,597 B2 | | 11/2015 | Bluemler et al. | |
| 9,314,207 B2 | * | 4/2016 | Marterstock | A61M 1/14 |
| 9,860,302 B2 | * | 1/2018 | Wittner | G16H 20/40 |

(Continued)

FOREIGN PATENT DOCUMENTS

| | | |
|---|---|---|
| WO | WO 2014/063798 A1 | 5/2014 |
| WO | WO 2017/108532 A1 | 6/2017 |

*Primary Examiner* — Elias Mamo
(74) *Attorney, Agent, or Firm* — Leydig, Voit & Mayer, Ltd.

(57) ABSTRACT

A medical device, such as a hemodialysis device or a peritoneal dialysis device includes a computation device, may be configured with an image-based support system, a method and/or a computer program for generating displayed instructional information for operation of the medical device. The computation device accesses a graphic memory on which instructional information is stored in a structured format having separately addressable sequences. An identification signal identifies individual sequences for dynamic display based on control data.

20 Claims, 2 Drawing Sheets

(56) References Cited

U.S. PATENT DOCUMENTS

| | | |
|---|---|---|
| 2006/0281063 A1 | 12/2006 | McClain |
| 2007/0156457 A1* | 7/2007 | Brown .................. A61B 5/044 |
| | | 705/2 |
| 2008/0263520 A1* | 10/2008 | Aguilar .................... G06F 8/33 |
| | | 717/125 |
| 2008/0320442 A1* | 12/2008 | Lyon-Smith .............. G06F 8/33 |
| | | 717/109 |
| 2009/0222119 A1 | 9/2009 | Plahey et al. |
| 2015/0139617 A1 | 5/2015 | Chakra |

\* cited by examiner

VIDEO-BASED UPGRADE OF DIALYSIS MACHINES

CROSS-REFERENCE TO RELATED APPLICATIONS

Priority is claimed to German Patent Application No. DE 102018108941.4, filed on Apr. 16, 2018, the entire disclosure of which is hereby incorporated by reference herein.

FIELD

The invention relates to a computation device, an image-based support system for a dialysis device or another medical device and a procedure as well as a computer program to generate displayed instructional information for operating support for a dialysis device or another medical device.

BACKGROUND

Medical devices, such as dialysis devices, often utilize a sequence of operating steps and actions to upgrade the medical device or for operation of the medical device, which have to be carried out on the medical device or on connected operating resources (e.g., a heparin pump). The operator is supported and guided while carrying out the operating steps by a suitable depiction on a display of the medical device. The display can be, for example, a touchscreen for the operating of the medical device and the input and output of data. A capacitive sensor technology may be used for the touch-sensitive user interfaces of the dialysis devices. A touchscreen with a capacitive sensor technology is, for example, described in U.S. Pat. No. 9,189,597, which is incorporated herein by reference.

A hemodialysis system comprises as a central unit a dialysis device which serves to continuously circulate a patient's blood in an extracorporeal circuit through a blood chamber of a filter or a dialyzer. The blood chamber is separated from a dialysis fluid chamber via a semi permeable membrane. A dialysis fluid containing blood electrolytes passes through the dialysis fluid chamber. The substance concentration of the dialysis fluid corresponds to the concentration of the blood of a healthy person. During the treatment, the blood of the patient and the dialysis fluid are circulated on respective sides of the membrane in general in a countercurrent manner with a predetermined flowrate. Substances that are typically excreted by urine diffuse through the membrane from the blood chamber into the chamber for dialysis fluid, while at the same time, electrolytes existent in the blood and the dialysis fluid diffuse from the chamber with the higher concentration into a chamber with lower concentration. The process can be additionally influenced by the application of a transmembrane pressure.

The extracorporeal blood circuit and the device itself comprise several components, such as pumps, valves, pressure sensors, as well as external contacts, push handles, blower filters, a busbar, hydraulic connections with flaps, etc. For upgrading or operating the dialysis device, these components may have to be operated in a coordinated sequence with several operating steps. During the execution of operating steps on the different technical operating resources of the dialysis device, operating errors can occur which impair the operating of the dialysis device or make it entirely impossible. It is thus important to ensure a correct and efficient operating. Errors should be detected and avoided.

It is known in the state of the art to issue certain guidance on a monitor of the dialysis device which support the operator during the execution of operating steps. The guidance can also comprise videos and/or animations.

With the familiar systems, it proves to be disadvantageous that the depiction of a video on the monitor can only be executed entirely. Often there are single passages or sections in a video that represent critical or difficult operating steps. The operator wants to request specific support specifically with these operating steps and is less or not interested in video sections shown before or after them. In order for the operator to be able to navigate to these critical points, they have to stop the whole video and repeat the respective section manually. This is associated with effort.

SUMMARY

In an exemplary embodiment, the invention provides a computation device for providing support during operation of a medical device. The computation device includes: a memory interface connected to a graphic memory, wherein instructional information is stored on the graphic memory in a structured format comprising individually addressed instructional sequences; and a processor configured to cause an identification signal for identification of at least one instructional sequence to be transmitted to the graphic memory via the memory interface for accessing the graphic memory and the at least one instructional sequence to be obtained from the graphic memory via the memory interface, and further to generate instructional information for display based on the at least one obtained instructional sequence.

In another exemplary embodiment, the invention provides a system for providing support during operation of a medical device. The system includes: a computation device and a monitor. The computation device includes: a memory interface connected to a graphic memory, wherein instructional information is stored on the graphic memory in a structured format comprising individually addressed instructional sequences; and a processor configured to cause an identification signal for identification of at least one instructional sequence to be transmitted to the graphic memory via the memory interface for accessing the graphic memory and the at least one instructional sequence to be obtained from the graphic memory via the memory interface, and further to generate instructional information for display based on the at least one obtained instructional sequence. The monitor is configured to display the generated instructional information for display.

In yet another exemplary embodiment, the invention provides a method for providing support during operation of a medical device. The method includes: providing, by a computation device, an identification signal to a graphic memory to access an instructional sequence identified by the identification signal, wherein instructional information is stored on the graphic memory in a structured format comprising a plurality of individually addressed instructional sequences; obtaining, by the computation device, the instructional sequence; and generating, by the computation device, instructional information for display based on the instructional sequence.

BRIEF DESCRIPTION OF THE FIGURES

Exemplary embodiments of the present invention will be described in even greater detail below based on the exemplary figures. The invention is not limited to the exemplary embodiments. All features described and/or illustrated herein can be used alone or combined in different combinations in embodiments of the invention. Features and advantages of various embodiments of the present invention will become apparent by reading the following detailed description with reference to the attached drawings which illustrate the following.

DETAILED DESCRIPTION

Figure 1:
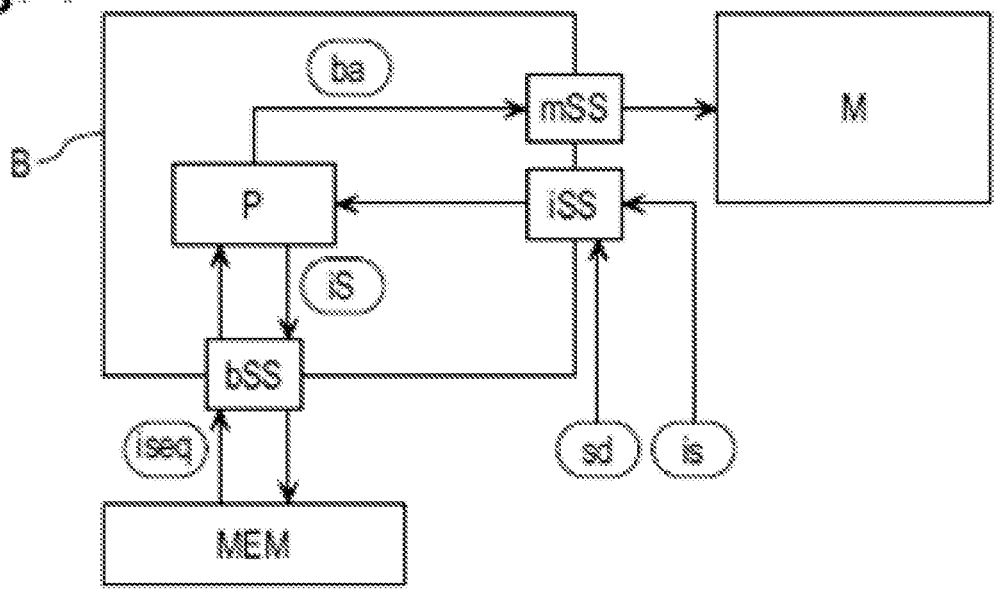
FIG. 1 shows in a schematic, overview-like representation a computation device for the generation of displayed instructional information for a monitor of a dialysis device or another medical device.

In order to give the operator more freedom and clearance with respect to viewing instructional guidance from a dialysis device, exemplary embodiments of the present invention provide for the ability to navigate specifically to particular instructional information.

The operating of medical devices goes along with the danger of contamination as soon as the operator has to execute entries on a touch-sensitive monitor. It is therefore desirable to minimize or eliminate user input for the operating of a display of assistance instructions.

Since the operating of a medical device may relate to life-sustaining measures for the patient, ensuring correct operation of the medical device with all preliminary steps is of high importance for patient safety. Exemplary embodiments of the invention enhance the human-machine interface in this context.

Exemplary embodiments of the invention enhance the operating of dialysis devices and improve safety. Furthermore, exemplary embodiments of the invention enhance and accelerate electronic support measures during the operating of the device, which can require several operating steps on potentially different operating resources. Exemplary embodiments of the invention provide an output result with enhanced image-based support via moving images, and can be operated without danger of contamination.

Exemplary embodiments of the invention include a computation device, a medical device with such a computation device, an image-based support system, a method, and a computer program.

In an exemplary embodiment, the invention provides a computer-based computation device for the generation of displayed instructional information (e.g., for a depiction on a monitor) to support operation of a medical device, such as a dialysis device undergoing a sequence of operating steps during an upgrade. In order to do that, the computation device exchanges data with a graphics memory via a memory interface. The graphics memory stores an amount of instructional information (e.g., videos with instructions on operating the device). The instructional information stored on the graphics memory is not saved monolithically or as a single block, but in sequences wherein each sequence has a structured format. The structured format allows for more flexible access to individual sequences of the instructional information, so that particular instructional sequences are addressable individually and independently of each other. The computation device provides an identification signal to identify at least one instructional sequence of the stored instructional information. The computation device can comprise a control interface configured to determine control data for the controlling of a display (e.g., to determine an output mode). Furthermore, the computation device may be configured to access the graphics memory with the identification signal in order to import the at least one instructional sequence corresponding to the identification signal and output the at least one identified instructional sequence on a display based thereon. The control interface may be contactless, which reduces the danger of contamination and germ transmission.

Exemplary embodiments of the invention provide an electronic module which can be used in combination with a medical device and which supports complex operating procedures with corresponding instructional sequences adapted to the operating time and the individual operating steps. An operating procedure (e.g., inserting a tube) comprises a sequence of operating steps which are to be carried out sequentially. Correspondingly, this is represented in the special formatting of the saved instructional information. Instructional information (e.g., an animated video) may correspondingly include a progression of instructional sequences. This provides the advantage that the user can be supported very specifically in their operating of the device. The chronological order and duration of the execution of the operating steps is therefore not tied to the chronological order and duration of the display of the instructional sequences (e.g., video sequences) and can be decoupled from it. This way, the user can carry out, for example, certain operating steps without video support or parallel to video output, and when it comes to complicated steps, the user can play the dedicated sequence several times.

In an exemplary embodiment of the invention, the control interface is a man-machine-interface (MMI) and is implemented in a way that germ transmission can be avoided. For example, the MMI may be a contactless interface (e.g., allowing gesture control, vibration-based control, and/or voice control). The MMI interface may also include an input element decoupled from other elements of the device (e.g., a foot switch) in order to avoid contamination.

The computation device controls a monitor for the output of displayed instructional information to support the operating of the device. The monitor can be connected to the medical device or integrated in the medical device. The monitor can be connected to the computation device as a separate device.

In an exemplary embodiment, the invention provides an image support system to support the operating of a medical device, such as a dialysis device, with:
 a monitor configured to display instructional information; and
 a computation device as described above, with the monitor being controlled by the computation device.

The monitor for the image support system can be connected to the medical device or integrated in the medical device. The control interface may be decoupled from the operating of the monitor (e.g., contactless).

Preferably, the medical device can comprise a sensor unit to determine an operating state of the device so that the identification signal can be determined from the determined operating state. For example, data obtained from the sensor unit can be used to determine whether the user has already carried out some operating steps and is now about to carry out a complicated operating step. From the sensor data of the sensor unit and with access to a rule base, the computation device can determine an instructional sequence corresponding to the determined operating state and to the following operating step. The rule base may include relationships between sensor data, metadata and instructional sequences.

It will be appreciated that features discussed herein with reference to one exemplary embodiment may also be applicable to other exemplary embodiments. For example, features relating to the exemplary configuration of devices described herein may also be applicable to corresponding methods carried out by such devices, and vice-versa.

In an exemplary embodiment, the invention provides a method for generating displayed instructional information to support the operating of a medical device, such as a dialysis device. A graphic memory is provided on which instructional information is stored in a structured formatting comprising a plurality of individually addressable instructional sequences. The method includes:

provide an identification signal for identification of an instructional sequence;

optionally determining control data to control a display;

accessing the graphic memory using the provided identification signal in order to import the identified instructional sequence;

generating instructional information for display based on the imported identified sequence and, optionally, further based on the control data. If no control data is determined or input accurately, pre-deposited standardized control data may be accessed.

In an exemplary embodiment of the invention, the identification signal is generated based on an operating state of the medical device as determined from sensor inputs. The operating state can be determined via a sensor unit. If, for example, the user is currently occupied with upgrading the peristaltic pump, this can be determined automatically via, for example, a visual sensor system. The identification signal for identifying instructional sequences corresponding to the operating procedure is determined based on the operating state (e.g., upgrading the peristaltic pump). Thus, the identification signal may be determined automatically and without user input. This has the advantage that the user is supported in their activity more efficiently without additional measures.

Three exemplary embodiments for the input of the identification signal are as follows:

1. The identification signal can be entered manually via a user input. To do that, there can be, for example, provided an interaction interface on a monitor (e.g., the monitor of the dialysis device) on which the user enters the identification signal (e.g., by using an input field on a touch sensitive display). In an exemplary embodiment, there can be different identifiers (e.g., graphic icons or names) displayed on the screen surface for that, from which the user can choose an input by clicking it. There could, for example, be displayed the identifiers of different sequences (e.g., via thumbnails) as a miniaturized graphic display of a sequence, which can comprise, for example, the first segment of the sequence. If the user chooses a thumbnail-display of a sequence, this sequence is seen as chosen and is passed on to the computation device as the identification signal or an identification data set.

2. An alternative embodiment for entering the identification signal is using so called metadata. Metadata are additional data which are saved on a memory with the sequences in an assigned way. There can be several metadata saved for one sequence. Metadata comprises, for example, temporal information (when a certain operating step is to be carried out), the respective to be controlled operating resource (e.g., peristaltic pump) and can comprise additional data sets if needed. An amount of metadata sets for each sequence is then filed in a memory of the computation device. This allows for a sequence to be identified by entering metadata as well. If the user chooses specific metadata from an amount of given metadata sets on a user interface, the metadata is registered and from that, an identification signal for identifying the sequence can be generated automatically. It is advantageous if the memory for the assigning of metadata and sequences is equipped with another interface to allow for the assigning to be changed independently of the procedure. With the additional interface, the procedure can be changed and can be adapted to the conditions of the respective user or the device.

3. A third embodiment for determining the identification signal is the automatic generation of the identification signal based on sensor data which are determined on the medical device. The sensor data may come from, for example, visual sensors and/or position sensors which are configured to determine an operating state of the device. For example, if one or more sensors indicate that the user has just started upgrading the device, the user is shown automatically one or more instructional sequences that correspond to the determined operating state and relate to the upgrading of the device.

In a further exemplary embodiment, after instructional information (e.g., in the form of an animation or a video) is already shown on a monitor, there can then be provided an additional interaction interface on the monitor via which the user can choose an instructional sequence that they want to see next. For that there can be displayed, for example, input fields corresponding to repeated display of the sequence, skipping, changing to the next sequence, changing to the previous sequence, jumping to the start of an instructional sequence, jumping to the end of an instructional sequence, and/or further control possibilities. In this embodiment, the screen display can comprise two segments:

1. an image segment configured to display an amount of identified sequences, and 2. an interaction interface, via which the user can control the display of the sequences (with orders such as FORWARD, STOP, SKIP etc.).

In an exemplary embodiment, control data may be determined. Alternatively predefined control instructions may be used. The control data may include an output mode for an identified instructional sequence (or multiple sequences). There may be multiple instructional sequences stored on a graphic memory corresponding to a certain operating procedure. The output mode indicates, for example, the form of the output for displaying the one or more instructional sequences on a monitor. The output mode may corresponding to a single sequence or a group of sequences. In one exemplary implementation, the output mode can indicate that initially one or more sequences are to be played in slow motion, and that one or more subsequent sequences are to be played at normal speed or at an accelerated speed. Additionally, the output mode can indicate, for example, that one or more particular instructional sequences are to be shown in a repeated loop. Additionally, there can be provided additional information on how often the action replays are to be shown. Furthermore, the control data can comprise additional data that indicates, for example, that the instruction information to be displayed includes additional data forms apart from video sequences, for example, data in textual from, audio files, etc.

In another exemplary embodiment of the invention, the control data is entered or determined via a contactless interface. The interface for determining the control data may be, for example, configured as an interaction interface. In another embodiment, two different interfaces can be utilized for determining the control data and determining the identification signal. Exemplary embodiments are described below with reference to the figures. The interface for entering the control data (control interface) can be, for example, an interface for determining gestures (visual interface) or an interface for determining speech input. This has the technical advantage that no direct touch is necessary to enter the control data. Accordingly, contaminations of the medical device or other elements can be avoided advantageously. Alternatively, control data can be determined locally on the computation device from imported data other than user input. Alternatively, pre-configured control data can be provided in a memory which—in case of missing or inaccurate input of the control data—can be used to generate instructional information for display.

Exemplary embodiments of the invention enable a user to choose relevant supporting operating guidance for display based on the temporal progress of operation, wherein the operating guidance corresponds to individually addressed instructional sequences. Furthermore, the user may choose an individual sequence out of a plurality of related sequences for display without requiring that all of the plurality of related sequences be displayed. Thus, for example, operating steps for which the user does not need support are not shown, while complicated operating steps for which the user would like image-based support can optionally be displayed in a freely selectable output mode (e.g., repeatedly or in slow motion). Accordingly, the user can adapt the display of supporting advice individually to their personal preferences. The individual sequences can be identified (and thus be displayed) separately, and different output modes can be determined for the respective sequences. An output mode can determine, for example, that a progression of sequences (which may correspond logically to a progression of to be carried out operating steps) is to be displayed. Thus, for the display, a transition or changing from a first sequence to a following sequence can be triggered automatically, as soon as the first sequence has been displayed in its entirety. Alternatively, the instructional guidance may stop automatically after carrying out a sequence, and the user may need to enter a trigger signal if the user wants to display another sequence. The trigger signal can, for example, be a part of the control data. For example, the trigger signal may correspond to the user pressing a FORWARD or BACK button. This prompts the execution of an incrementing or decrementing order in the memory, so that a correspondence next or previous sequence is displayed. Stopping the instructional guidance automatically after each sequence has the advantage that it is possible to minutely adapt the screen display temporally. In a further exemplary embodiment, the user is given an option to either activate or deactivate the automatic playing of a next sequence in a progression of sequences (e.g., using a start signal for activation and/or using a stop signal for deactivation). This has the advantage of minimizing required user interventions while still giving the user flexible control over the display.

In another exemplary embodiment of the invention, in addition to sequences being stored on the graphic memory, corresponding metadata is also stored. In this manner, a sequence can be addressed or identified not only directly via its memory address in the memory, but also via the corresponding metadata. The graphic memory can thus be implemented, for example, in the form of a relational database, and access to the database may be based on the identification signal as well as a parameter of the metadata. This allows, for example, a single query to be used to identify all sequences relating to a particular operating resource (e.g., a dialysate container) and to output the query results to the display.

As discussed above, individual sequences of the instructional information can be addressed independently of each other and uniquely identified. In an exemplary embodiment, the sequences are segmented in the graphic memory via a procedure for non-linear editing.

Exemplary embodiments of the invention may be computer-implemented and may include procedures carried out in the computation device. For example, a computer program is loaded on an internal memory of the computation device and comprises software routines for carrying out the operations discussed herein. Thus, exemplary embodiments of the invention also include computer programs and processor-executable instructions stored on a non-transitory computer-readable medium.

In another exemplary embodiment, a computer program product for a medical device is loaded into the memory of a computer or an electronic or medical device or is loadable with a computer program that can be loaded onto an internal memory of a digital control unit.

Operating a medical device may include operations concerning different operating resources of the medical device and may include a progression of operating steps that are to be carried out consecutively, which are carried out on the same or different operating resources. In order to support the user during operation of the medical device, a display may output instructional guidance which is generated based on an identification signal and/or based on control data. Exemplary operations include, for example, operations relating to upgrading the medical device. The medical device may be, for example, a blood treatment device, a hemodialysis device, a peritoneal dialysis device, or another type of medical device. The display comprises a graphic element configured to display one or several identified instructional sequences.

The instructional sequences may include sequences of images, video sequences, single frames of a video, animations, or other instructional information. An instructional sequence may also include a moving picture that can be enhanced with additional data, such as text data (e.g., animations with overlaid textual guidance).

The instructional information may include video segments. The instructional information may be structured such that it includes a progression of sequences, with the individual sequences corresponding to different operating steps and being individually and independently addressable.

Operating the medical device may include a progression of individual operating steps. The instructional information may thus be structured to include a progression of instructional sequences corresponding to the progression of operating steps. To generate the sequences and to save them on the graphic memory, different approaches can be used. For example, an individual sequence may be a relatively short video segment from a longer video based on predefined rules. For example, the length of the extracted segment may be adapted to the operating step that is to be carried out, and the extraction may be based on a rule base with rules that define the length of the sequences and/or the content of the sequences. For example, a first sequence can comprise first, second and third images, while a second sequence comprises fourth and fifth images, and a third sequence comprises sixth, seventh, eighth, ninth and tenth images.

User input (e.g., of control data and/or an identification signal) may be received in a contactless manner (e.g., via voice entries or gestures), in order to avoid germ transmission. Alternatively, a foot switch can be provided for simple operating measures (e.g., operating a foot switch can be provided for the advancing from one sequence to the next).

An identification signal may be data which identifies a graphic memory address (e.g., register) corresponding to a stored sequence.

The control data may control the display. The control data may indicate an output mode for the identified sequence. The output mode may include several parameters, such as output speed (slow motion, accelerated, etc.), resolution, and other parameters (e.g., relating to a particular image section or an output direction of the sequence (relative to the temporal progression, such as forwards or backwards)).

The computation device may include hardware such as an integrated circuit (e.g., a field-programmable gate array (FPGA)) and/or software. The computation device is configured to generate the output for the display. The computation device can be implemented directly in a graphic board or in a graphic chip or indirectly on a processor which is in data exchange with the graphic board and a monitor. The graphic board writes data for the monitor on a graphic memory which is may be a random access memory (RAM). The processor and/or the graphic chip or the graphic board read out the memory in order to display the saved data—e.g., via a digital-analog (D/A) converter—on the display. A video adapter may be implemented which uses the digital signals of the computation device and/or of an application program, saves them on the memory (e.g. video RAM) and converts them into analog signal (using a D/A converter). The computation device is configured to facilitate display of a dynamically-generated output for the monitor. The display can be controlled based on sensor data of a sensor unit dependent on an operating progress or state of a corresponding medical device. The control data may include control commands for the monitor generated via control logic of the computation device.

The sensor unit may include several sensor modules. The sensor modules may include several sensors. The sensor modules may be built into a dialysis device, for example in several places on the dialysis device and in all or selected operating resources of the dialysis device and/or in the respective interfaces between the dialysis device and an operating resource thereof. The sensors include, for example, sensors of different sensor types, such as optical sensors, acoustic sensors, position and/or approximation sensors, temperature sensors, resonance sensors, switches, calipers, potentiometers, etc.

The medical device may include a plurality of operating resources, such as pumps, tubes, dialysis filters in dialyzers, clamps and other mechanical and/or electronic components which have to be connected to the device or are integrated into the device. The operating resources can be configured to collect disposables, such as tubes, filters, disposable syringes, etc. According to an exemplary embodiment, each operating resource is configured with at least one sensor. The operating resources are to be operated. A heparin syringe, for example, is to be inserted and connected correctly into a corresponding heparin pump in the device. This may correspond to a progression of specific operating steps relating to the device and/or the operating resources. Status of the progression is detected by the sensor unit according to an exemplary embodiment. Obtained sensor signals may represent the operating state of the device and its operating resources. An upgrade of a dialysis device with a blood tube system can be carried out, for example, only when the cap is open. For that, an instructional sequence may be output (e.g., via textual instructional information) which indicates that the cap is to be opened.

Exemplary embodiments of the invention provide that individual instructional sequences may be independently used for output on a display. Further, for each of the individual sequences, different output modes can be provided. For example, a first sequence can be displayed slowly, a second sequence displayed repeatedly, and a third sequence displayed in an accelerated manner. In other words, the output of individual sequences can be provided independently of each other and with different output modes.

Another advantage is that the display can be changed dynamically during output. For example, control data may be received via user input and/or otherwise changed, so as to modify what is displayed. For example, if a particular sequence is being displayed in a first output mode (normal display), and the user signals with new control data that a different output mode is to be used (e.g., slowed down display), the computation device may generate a corresponding control command to cause the sequence to be output in slow motion. Additionally, after a particular sequence is complete, the user may be presented with further options such as displaying the sequence again or changing to another sequence. The control data can be specific to an individual sequence in order to be able to display different output modes for a particular individual sequence. Arbitrary jumps from one sequence to another that do not necessarily correspond to a sequential progression of operating steps can be carried out as well. This allows the user to flexibly choose which sequence is to be displayed, including for example already carried out and implemented sequences.

In an exemplary embodiment, control data and/or an identification signal can comprise more extensive parameters so that, for example, time frames can be defined for displaying particular sequences. The time frames may correspond to time frames for carrying out operating steps of an operating procedure. In another example, further parameters can be determined corresponding to the appearance of the display. For example, there may be parameters relating to zoom defaults or defaults for a level of detail, or for enhancing or reducing the level of detail (e.g., via resolution or zoom) in animations.

Exemplary embodiments of the invention provide improvements with respect to the man-machine-interface of a medical device with regard to the provisions of instructional information in a manner which will help to reduce or eliminate operating errors.

FIG. 1 is a schematic representation of an electrical or computer-based computation device B for the generation of displayed instructional information for a monitor M of a dialysis device or another medical device. The computation device B comprises a processor P for data processing. In an exemplary embodiment, the computation device B comprises three different interfaces: a monitor interface mSS, an interaction interface iSS and a memory interface bSS. The processor generates instructional information for display ba which is sent to the monitor M of the dialysis device via the monitor interface mSS. For generating the instructional information for display ba, the computation device B utilizes input data. The input data can include an identification signal (is) and/or control data sd. The control data sd and the identification signal (is) can be determined via a common interface, such as via the interaction interface iSS. The interaction interface iSS may be a contactless interface such as a gesture interface or a speech input interface. The interaction interface iSS is a user interface. The data determined by the interaction interface iSS is forwarded to the processor P for processing. In an alternative embodiment, the control data sd may be determined on another interface separate from an interface through which the identification signal (is) is received. Furthermore, it is possible that the control data sd is generated on the processor P of the computation device B. The identification signal may include a data set for identifying a memory address in a graphic memory MEM. In this case, the identification signal (is) can be used to directly access an address on the graphic memory MEM. Alternatively, the identification signal can comprise a data set which indicates certain parameters of metadata. In this case, the determined metadata is forwarded to the processor P, which then determines an identification signal (iS) on the basis of predefined rules which can be deduced from a rule base. The processor then accesses the graphic memory MEM based on the identification signal (iS) in order to identify one or more sequences out of a plurality of sequences saved therein and forwards the identified sequence(s) iseq to the processor P. Upon receiving the identified sequence(s) iseq, the processor P generates instructional information for display ba and forwards the instructional information for display to the monitor M via the monitor interface mSS. The instructional information for display is then displayed on the monitor M. In the embodiment of FIG. 1, the dialysis device is implemented as a separate entity relative to the computation device B. This has the advantage that a respective user can use, for example, a user-specific monitor M (e.g., a mobile radio unit or another mobile device), on which applications are implemented in order to manage the data exchange with the computation device B as well as receive the control signals via the monitor interface mSS for the instructional information for display ba. The graphic memory MEM comprises a plurality of instructional sequences, including for example, videos, animations, or individual images. Each instructional sequence may corresponding to a respective operating action for the dialysis device, relating to, for example, upgrading, operating, and/or maintaining the dialysis device. The instructional information may include a video. The video is not saved monolithically on the graphic memory MEM, but rather is pre-processed. For example, each video may be segmented into a progression of instructional sequences using a procedure for non-linear editing. For example, a video may be segmented into m segments, wherein the first segment comprises instructional sequences seq1_1, seq1_2, . . . seq1_n, the second segment comprises instructional sequences seq2_1, seq2_2, . . . seq2_n, and an mth segment comprises instructional sequences seqm_1, seqm_2, . . . seqm_n. Hereby, a single instructional sequence can correspond to a single operating step or a plurality of operating steps. Sequences may be extracted from a video segment, for example, using a rule base which determines the parameters that are to be followed when segmenting a video into video segments and further into instructional sequences.

Exemplary embodiments of the invention thus allow a user to flexibly control the display of instructional information corresponding to operating steps being performed relative to a dialysis device. It is then no longer necessary to stop a monolithic video and rewind it manually in order to display the respective operating step repeatedly. Segmenting of a video into sequences allows a user to select individual sequences for display via corresponding control data.

Figure 2:
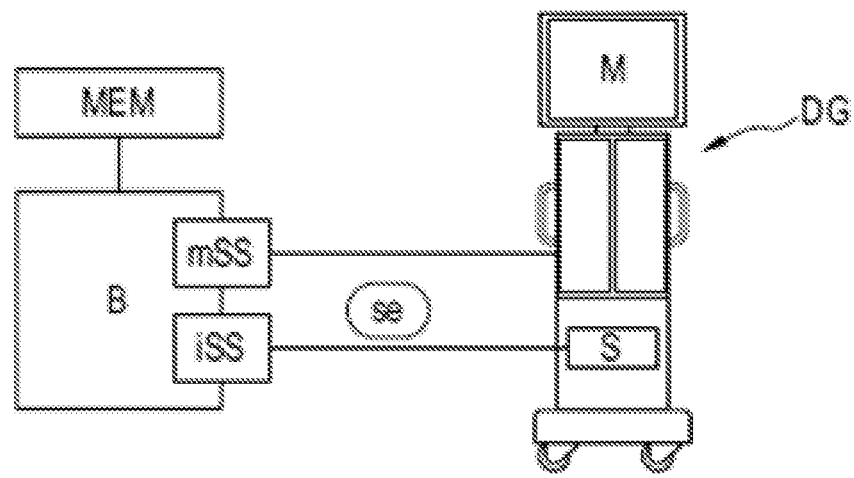
FIG. 2 shows an alternative embodiment of a computation device for a dialysis device.

FIG. 2 shows an exemplary embodiment of a computation device B and a dialysis device DG. The computation device DG includes three interfaces in accordance with the example represented in FIG. 1: the monitor interface mSS, the interaction interface iSS and the memory interface bSS. The instructional information for display ba is forwarded to the monitor M of the dialysis device DG via the monitor interface mSS. In this case, the monitor M for the screen display is integrated into the dialysis device DG. The computation device B accesses the graphic memory MEM for determining the identified sequence(s) iseq in order to generate the instructional information for display ba on the basis of the identified sequence(s) iseq and the control data sd. As shown schematically in FIG. 2, the dialysis device DG comprises additionally a sensor unit S which can include several different sensor types (e.g., position sensors, pressure sensors, visual sensors, etc.). The sensor unit S is configured to determine sensor data se which can be forwarded to the processor P of the computation device B via the interaction interface iSS. The sensor data se indicates an operating state of the dialysis device DG. For example, it can be determined automatically which steps have already been carried out for operating the device and which ones have still to be carried out. On the basis of the sensor data se, the processor P can determine the identification signal (is) by accessing a databank. The identification signal (is) is then used to access the graphic memory MEM in order to determine relevant sequence(s) for dynamically determining the instructional information for display ba.

Figure 3:
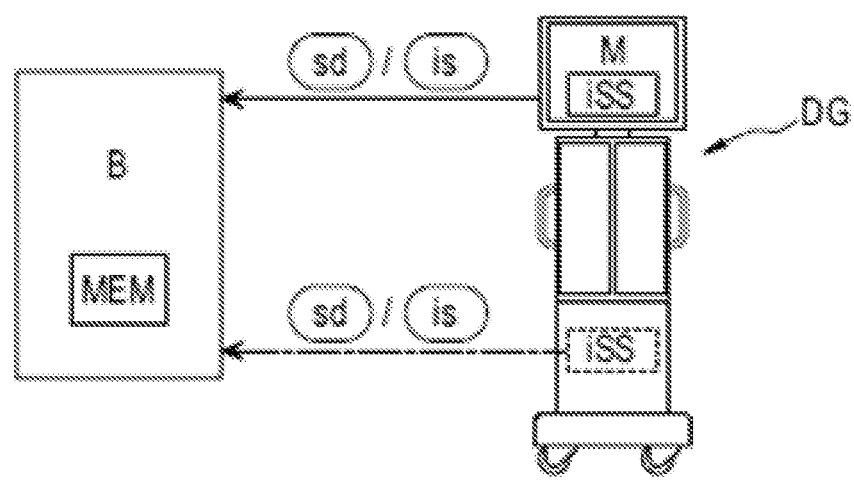
FIG. 3 refers to another embodiment for a computation device with a modified configuration of components.

FIG. 3 shows an exemplary embodiment of a computation device B and a dialysis device DG, in which the graphic memory MEM is integrated into the computation device B. In accordance with the embodiment shown in FIG. 2, the monitor M is configured for displaying instructional information ba and is integrated in the dialysis device DG. The interaction interface iSS is also implemented in the dialysis device DG as well. The interaction interface iSS may be, for example, the user interface on a touch sensitive display (of the monitor M) (shown in FIG. 3 with the continuous line). Alternatively, at least a part of the interaction interface iSS may be configured to determine interaction signals in a contactless manner and may be configured, for example, as a foot switch or a gesture interface (shown in FIG. 3 with the dotted line). The interaction interface iSS may be configured to receive control data sd and/or an identification signal (is) and to forward the control data sd and/or the identification signal (is) to the computation device B. The computation device B receives the control data sd and/or the identification signal (is) via an interface (e.g., via the monitor interface mSS) and dynamically generates instructional information for display by accessing the graphic memory MEM and transferring the instructional information for display to the dialysis device DG via the monitor interface mSS.

Figure 4:
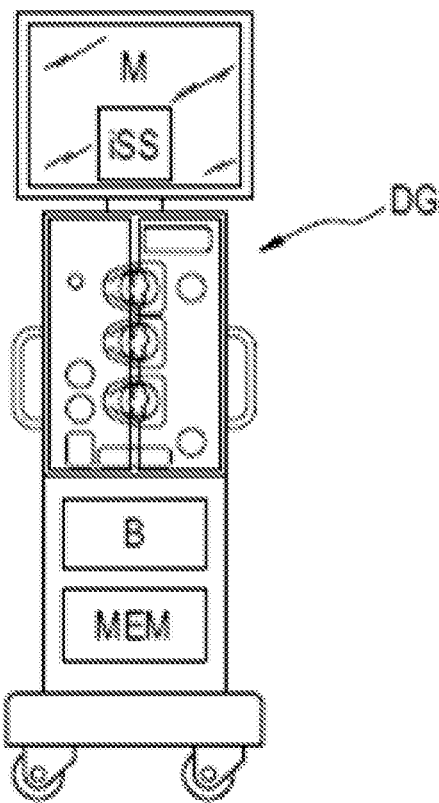
FIG. 4 shows another alternative in which the computation device is integrated into a medical device.

Another embodiment is shown in FIG. 4. Here, all of the elements of the image-based support system, including the monitor M, the computation device B and the graphic memory MEM are integrated in the dialysis device DG. In this example, the interaction interface iSS is implemented as a graphical user interface on the touch sensitive monitor M. The interaction interface iSS may also be implemented as a contactless interface, for example, which receives gestures in order to configure the instructional information for display ba. The configuration of the system is flexible, such that the described functionalities can be distributed in another configuration. For example, it is possible to modify FIG. 4 by having the graphic memory MEM be implemented as a separate module accessible via respective interfaces.

Figure 5:
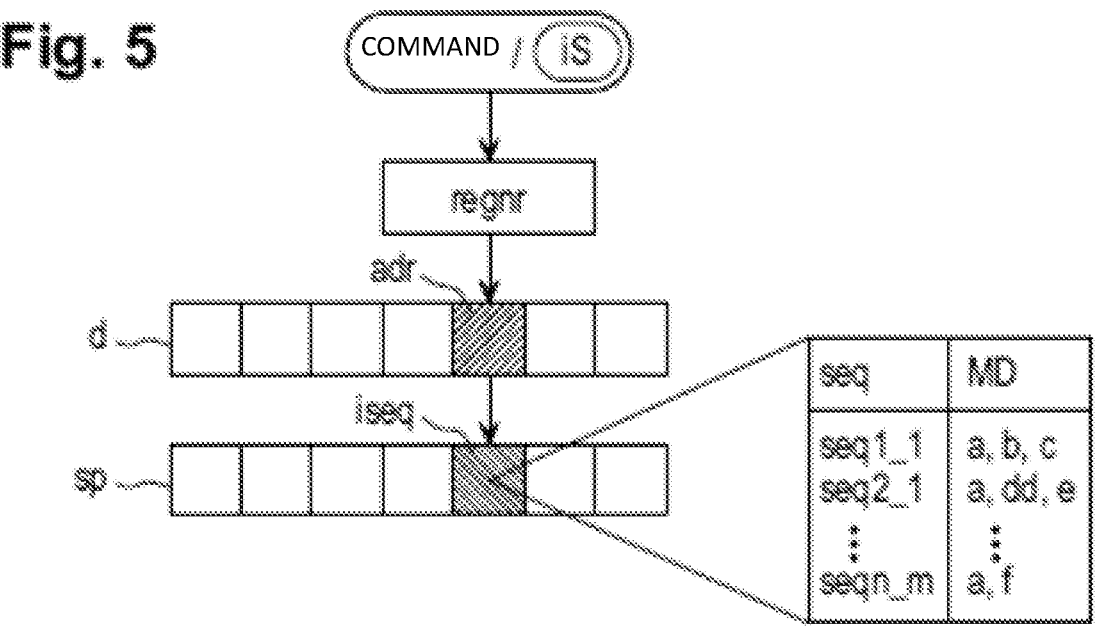
FIG. 5 shows a more detailed schematic representation of a graphic memory on which instructional sequences are not saved monolithically but in a specifically structured format.

FIG. 5 shows in a schematic representation that instructional information (such as a video) is not archived as a monolithic file in the graphic memory MEM, but rather as a plurality of instructional sequences seq, which can be independently identified by the computation device B. For example, an identification signal (iS) may correspond to a command for access. This command accesses a register number which has the reference sign regnr in FIG. 5. With the register number regnr, a specific access onto an element of a register file d can be carried out in order to identify a certain address field adr. Via the address field adr, the memory can be accessed in order to determine an identified sequence iseq which is forwarded to the processor P of the computation device B. Depending on the implementation, the address adr can refer directly or indirectly to the element on the memory. As shown schematically on the right side of FIG. 5, a memory element can comprise an assignment of respective sequences seq to another data set, metadata MD. Each respective sequence corresponds to respective metadata MD. For example, as depicted in FIG. 5, the sequence seq1_1 is assigned metadata a, b, c; the sequence seq2_1 is assigned metadata a, d, e; and the sequence seqn_m is assigned metadata a, f. Accordingly, a sequence may be retrieved by querying parameters of the metadata MD. The memory MEM can be a physical or a virtual memory. It is also possible that the graphic memory MEM is assigned to the dialysis device DG or is integrated into it.

Figure 6:
FIG. 6 shows a flow chart of a procedure according to an exemplary embodiment of the invention.

In connection with FIG. 6, a procedure according to an embodiment is described in greater detail.

After starting the procedure, an identification signal for the identification of a sequence seq is provided in step S1. The identification signal (is) can either be entered manually via a user interface (e.g., the interaction interface iSS) or it can be determined automatically from existing data (e.g., the identification signal can be determined from control data sd or metadata MD). The metadata MD may be user input via a user interface.

In step S2, control data sd for controlling a display ba is determined. This can be done via the interaction interface iSS, which may be a contactless interface.

Then follows an access onto the graphic memory MEM by the computation device B using the provided identification signal (is). This occurs in step S3. In the following step S4, the identified sequence iseq corresponding to the identification signal is obtained by the computation device B.

In step S5 the instructional information for display ba is determined dynamically on the processor P of the computation device B after receiving the identified sequence iseq. For example, the obtained identified sequence iseq is used in order to generate the instructional information for display ba dynamically on the basis of control data sd. The instructional information for display is then forwarded to the monitor M via the monitor interface mSS.

Since instructional information for operating support is advantageously subdivided into sub-steps (e.g., sequences seq), it is possible to get from one display of a sequence seq on the monitor M respectively to the next sequence seq via a respective trigger signal (e.g., using a foot switch, an arrow key or a gesture). Transitioning from one sequence to the next can also occur automatically, for example, based on identifying sequences relevant to an operating state of the dialysis device DG based on sensor data from a sensor unit S. For example, if a sensor on the sensor unit S determines that an alpha clip on a blood pump has been crushed, a corresponding sequence of operating instructions may be automatically identified.

Sequences seq may be saved in a GIF-format.

In an exemplary embodiment, the sensor unit S is configured to measuring time such that operating times corresponding to operating steps may be measured. The measured operating time for each operating step is delivered to a digital processing unit. Based on detecting that a longer time interval is needed for carrying out an operating step, a corresponding control signal of the control data sd can be generated in order to instruct the computation device B to slow down a displayed sequence seq. Thus, the displayed instructional information ba can be adapted dynamically to the temporal progress of user operations without the user having to enter user inputs. Additionally, if it is determined that the user carries out operating steps relatively quickly, a corresponding control signal may be generated in order to display instructional information ba faster.

In the first case, if a slowed down execution is determined, further support measures can be triggered (e.g., the displayed information ba can comprise an additional element which asks the user if further supporting instructions (e.g., in the form of text and/or sound) are desired). If the user confirms this via a corresponding user input, measures are triggered automatically in order to issue further instructions in connection with the respective operating step. The instructions can be issued in graphic, textual and/or audio form. Furthermore, it is possible to access a knowledge database via another network interface in order to provide further instructions.

In an exemplary embodiment the generating of the displayed instructional information occurs dynamically and based on user input. For example, the user can accelerate or slow down the displayed instructional information ba. These user inputs may be provided with respect to individual sequences, which provides the user with flexibility.

In an exemplary embodiment of the invention the dynamically generated instructional information for display ba comprises a progression of identified sequences iseq. In this progression of identifies sequences iseq there can be set additional trigger points in order to determine trigger signals of the user in order to control the instructional information for display ba. Thus, it can be determined at a trigger point that the previous sequence is to be repeated again or it can be determined that the following sequence is to be displayed. It can be determined as well at a trigger point to jump to an arbitrary future sequence and thus skip other sequences. In other words, the trigger points may determine control data sd. The control data sd may be determined via user input, for example, provided in a contactless manner in order to minimize the danger of germ transmission.

In another embodiment, the control data sd can define whether the identified sequences iseq are to be played as a visual format only (visual display only) or additionally with sound as well. The playback of the identified video sequence iseq without sound can be seen as useful, for example, when the dialysis device DG is to be used in a dialysis center having several dialysis devices DG in one room in order to minimize noise for patients in the room.

It will be appreciated that the embodiments described herein are exemplary. In certain other exemplary embodiment, other interfaces may be provided for determining the input data for the computation device apart from the interaction interface. Additionally, it will be appreciated that the principles discussed herein may apply to other medical devices other than dialysis devices.

It will further be appreciated that exemplary embodiments of the invention may include various different configurations of the described components, for example, in an integrated configuration (e.g., as shown in FIG. 4) or in a distributed configuration (e.g., as shown in FIGS. 2-3).

It will be appreciated that the execution of the various machine-implemented processes and steps described herein may occur via the execution, by one or more respective processors, of processor-executable instructions stored on a tangible, non-transitory computer-readable medium, such as random access memory (RAM), read-only memory (ROM), programmable read-only memory (PROM), and/or another electronic memory mechanism. Thus, for example, operations performed by a medical device or a computation device as discussed herein may be carried out according to instructions stored on and/or applications installed on one or more respective computing devices.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A computation device for providing support during operation of a medical device, the computation device comprising:
   a memory interface connected to a graphic memory, wherein instructional information is stored on the graphic memory in a structured format comprising individually addressed instructional sequences; and
   a processor configured to:
      determine, based on sensor data from one or more sensors, that a current operating state of the medical device corresponds to a component of the medical device being upgraded;
      generate an identification signal for identification of at least one instructional sequence based on the current operating state of the medical device, wherein the at least one instructional sequence relates to upgrading the component of the medical device;
      cause the identification signal to be transmitted to the graphic memory via the memory interface for accessing the graphic memory and the at least one instructional sequence to be obtained from the graphic memory via the memory interface; and
      generate instructional information for display based on the at least one obtained instructional sequence.

2. The computation device according to claim 1, further comprising:
   an interaction interface configured to receive user input in a contactless manner.

3. The computation device according to claim 1, further comprising:
   an interaction interface configured to receive control data via user input;
   wherein generating the instructional information for display is further based on the control data.

4. A system for providing support during operation of a medical device, the system comprising:
   a computation device comprising:
      a memory interface connected to a graphic memory, wherein instructional information is stored on the graphic memory in a structured format comprising individually addressed instructional sequences; and
      a processor configured to: determine a current operating state of the medical device based on sensor data from one or more sensors, wherein the current operating state corresponds to the medical device being upgraded or a problem with the medical device; generate an identification signal for identification of at least one instructional sequence based on the determined current operating state of the medical device, wherein the at least one instructional sequence relates to upgrading the medical device or the problem with the medical device; cause the identification signal to be transmitted to the graphic memory via the memory interface for accessing the graphic memory and the at least one instructional sequence to be obtained from the graphic memory via the memory interface; and generate instructional information for display based on the at least one obtained instructional sequence; and
   a monitor configured to display the generated instructional information.

5. The system according to claim 4, wherein the monitor is connected to the medical device or is integrated in the medical device.

6. A method for providing support during operation of a medical device, the method comprising:
   determining, by a computation device, based on sensor data from one or more sensors, that a current operating state of the medical device corresponds to a problem with a component of the medical device;
   generating, by the computation device, an identification signal for identification of at least one instructional sequence based on the current operating state of the medical device, wherein the at least one instructional sequence corresponds to the problem;
   providing, by the computation device, the identification signal to a graphic memory to access the at least one instructional sequence identified by the identification signal, wherein instructional information is stored on the graphic memory in a structured format comprising a plurality of individually addressed instructional sequences;
   obtaining, by the computation device, the at least one instructional sequence; and generating, by the computation device, instructional information for display based on the at least one instructional sequence.

7. The method according to claim 6, further comprising: determining control data;
wherein generating the instructional information for display is further based on the control data.

8. The method according to claim 6, wherein the identification signal is based on a previously identified instructional sequence.

9. The method according to claim 6, wherein the identification signal is determined based on a user query for metadata corresponding to one or more instructional sequences.

10. The method according to claim 6, wherein each individually addressed instructional sequence has corresponding metadata stored on the graphic memory such that each individually addressed instructional sequence is identifiable via corresponding metadata.

11. The method according to claim 6, wherein the identification signal is determined based on a user selection of an identifier corresponding to a sequence.

12. The method according to claim 6, wherein generating the instructional information for display is further based on control data indicating an output mode for the at least one instructional sequence.

13. The method according to claim 6, further comprising: receiving control data via a contactless interface.

14. The method according to claim 6, further comprising: detecting a start signal; and/or
detecting a stop signal.

15. The method according to claim 6, wherein the at least one instructional sequence corresponds to at least one operating step for operating the medical device.

16. The method according to claim 6, wherein the at least one instructional information is segmented into the plurality of individually addressed instructional sequences via non-linear editing.

17. The computation device according to claim 1, wherein generating the identification signal is further based on a rule base including relationships between sensor data, metadata and instructional sequences.

18. The computation device according to claim 1, wherein the one or more sensors comprise a visual sensor system.

19. The computation device according to claim 1, wherein the sensor data includes a measurement of an amount of time for carrying out an operating step, and wherein the processor is further configured to slow down the display of the instructional information based on the measurement of the amount of time for carrying out the operating step.

20. The computation device according to claim 1, wherein the sensor data indicates that one or more steps have been carried out for operating the medical device.

\* \* \* \* \*